(12) United States Patent
Horwitz

(10) Patent No.: US 7,440,115 B2
(45) Date of Patent: *Oct. 21, 2008

(54) SYSTEM AND METHODS FOR WAVEFRONT MEASUREMENT

(75) Inventor: Larry S. Horwitz, Seal Beach, CA (US)

(73) Assignee: Ophthonix, Inc., Vista, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/371,038

(22) Filed: Mar. 8, 2006
(Under 37 CFR 1.47)

(65) Prior Publication Data

US 2007/0002332 A1    Jan. 4, 2007

Related U.S. Application Data

(63) Continuation of application No. 10/314,906, filed on Dec. 9, 2002, now Pat. No. 7,034,949, which is a continuation-in-part of application No. 10/014,037, filed on Dec. 10, 2001, now Pat. No. 6,781,681.

(51) Int. Cl.
*G01B 9/02* (2006.01)

(52) U.S. Cl. ................................................. 356/512

(58) Field of Classification Search .............. 356/124.5, 356/515, 512, 521, 514
See application file for complete search history.

(56) References Cited

U.S. PATENT DOCUMENTS

| | | | |
|---|---|---|---|
| 4,105,302 A | 8/1978 | Tate, Jr. |
| 4,670,646 A | 6/1987 | Spivey |
| 4,711,576 A | 12/1987 | Ban |
| 5,062,702 A | 11/1991 | Bille |
| 5,080,477 A | 1/1992 | Adachi |
| 5,164,750 A | 11/1992 | Adachi |
| 5,528,321 A | 6/1996 | Blum et al. |
| 5,777,719 A | 7/1998 | Williams et al. |

(Continued)

FOREIGN PATENT DOCUMENTS

DE        42 22 395        1/1994

(Continued)

OTHER PUBLICATIONS

Barsky et al., *Incorporating Camera Models, Ocular Models, and Actual Patient Eye Data for Photo-Realistic and Vision-Realistic Rendering*, Fifth Int'l. Conf. on Mathematical Methods for Curves and Surfaces, Oslo, Jun. 29, 2000, "Mathematical Methods in CAGD," Vanderbilt University Press, Nashville, 2001 1-10.

(Continued)

*Primary Examiner*—Hwa (Andrew) S Lee
(74) *Attorney, Agent, or Firm*—Morrison & Foerster LLP

(57) ABSTRACT

A method and apparatus for characterizing an object with a wavefront from the object is disclosed. In one embodiment, the apparatus includes: a reticle positioned in a path of the wavefront, the reticle comprising two superimposed linear grating patterns; at least one light detector positioned relative to the reticle to receive a self-image diffraction pattern of the reticle produced by the wavefront; and at least one processor receiving signals from the light detector representative of the self-image diffraction pattern and deriving derivatives associated therewith, the processor using the derivatives to characterize said object.

92 Claims, 5 Drawing Sheets

U.S. PATENT DOCUMENTS

| | | |
|---|---|---|
| 5,898,479 A | 4/1999 | Hubbard et al. |
| 5,929,970 A | 7/1999 | Mihashi |
| 5,949,521 A | 9/1999 | Williams et al. |
| 5,963,300 A | 10/1999 | Horwitz |
| 6,007,204 A | 12/1999 | Fahrenkrug et al. |
| 6,050,687 A | 4/2000 | Bille et al. |
| 6,086,204 A | 7/2000 | Magnante |
| 6,095,651 A | 8/2000 | Williams et al. |
| 6,112,114 A | 8/2000 | Dreher |
| 6,120,150 A | 9/2000 | Sarver et al. |
| 6,155,684 A | 12/2000 | Bille et al. |
| 6,199,986 B1 | 3/2001 | Williams et al. |
| 6,234,631 B1 | 5/2001 | Sarver et al. |
| 6,256,098 B1 | 7/2001 | Rubinstein et al. |
| 6,257,723 B1 | 7/2001 | Sarver et al. |
| 6,270,221 B1 | 8/2001 | Liang et al. |
| 6,271,915 B1 | 8/2001 | Frey et al. |
| 6,299,311 B1 | 10/2001 | Williams et al. |
| 6,305,802 B1 | 10/2001 | Roffman et al. |
| 6,309,068 B1 | 10/2001 | Kohayakawa |
| 6,338,559 B1 | 1/2002 | Williams et al. |
| 6,379,005 B1 | 4/2002 | Williams et al. |
| 6,379,008 B1 | 4/2002 | Chateau et al. |
| 6,382,795 B1 | 5/2002 | Lai |
| 6,394,605 B1 | 5/2002 | Campin et al. |
| 6,396,588 B1 | 5/2002 | Sei |
| 6,460,997 B1 | 10/2002 | Frey et al. |
| 6,499,843 B1 | 12/2002 | Cox et al. |
| 6,550,917 B1 | 4/2003 | Neal et al. |
| 6,554,429 B1 | 4/2003 | Campin et al. |
| 6,573,997 B1 | 6/2003 | Goldberg et al. |
| 6,607,274 B2 | 8/2003 | Stantz et al. |
| 6,736,510 B1 * | 5/2004 | Van Heugten ............... 351/221 |
| 6,781,681 B2 | 8/2004 | Horwitz |
| 6,786,602 B2 | 9/2004 | Abitbol |
| 2001/0033362 A1 | 10/2001 | Sarver |
| 2001/0035939 A1 | 11/2001 | Mihashi et al. |
| 2001/0041884 A1 | 11/2001 | Frey et al. |
| 2002/0047992 A1 | 4/2002 | Graves et al. |
| 2002/0122153 A1 | 9/2002 | Piers et al. |
| 2002/0140902 A1 | 10/2002 | Guirao et al. |
| 2002/0167643 A1 | 11/2002 | Youssefi |
| 2002/0186346 A1 | 12/2002 | Stantz et al. |
| 2002/0196412 A1 | 12/2002 | Abitbol |
| 2003/0011745 A1 | 1/2003 | Molebny et al. |
| 2003/0151721 A1 | 8/2003 | Lai et al. |

FOREIGN PATENT DOCUMENTS

| | | |
|---|---|---|
| EP | 1 153 570 | 11/2001 |
| WO | WO-92/01417 | 2/1992 |
| WO | WO-98/27863 | 7/1998 |
| WO | WO-99/66308 | 12/1999 |
| WO | WO-00/10448 | 3/2000 |
| WO | WO-00/19885 | 4/2000 |
| WO | WO-01/47449 | 7/2001 |
| WO | WO-01/58339 | 8/2001 |
| WO | WO-01/82791 | 11/2001 |
| WO | WO-01/89424 | 11/2001 |
| WO | WO-02/09579 | 2/2002 |
| WO | WO-02/19901 | 3/2002 |
| WO | WO-02/28272 | 4/2002 |
| WO | WO-02/30273 | 4/2002 |
| WO | WO-03/009746 | 2/2003 |

OTHER PUBLICATIONS

Kung, Micro-Optical Wavelength Detectors, http://clynlish.stanford.edu/~hlkung/research.html, printed Jun. 9, 2003, 3 pages.

Liang et al., *Objective measurement of wave aberrations of the human eye with the use of a Hartmann-Shack wave-front sensor*, *Journal of Optical Society of America*, vol. 11, No. 7, Jul. 1994, 1949-1957.

Naulleau et al., Journal of Vacuum Science Technology (2000) vol. B 18, No. 6, Nov./Dec. pp. 2939-2943.

Ohba, *Wavefront* Sensor Using a 2-Dimensional Diffraction Grating, *Japanese Journal of Applied Physics*, vol. 37, 1998, pp. 3749-3753.

Platt et al., "History and Principles of Shack-Hartmann Wavefront Sensing," Journal of Refractive Surgery, vol. 17, Sep./Oct. 2001.

SPIEWeb Scholarly Journals, Optical Engineering, vol. 38, No. 12, Dec. 1999.

Supplementary European Search Report for EP 02 79 7270, mailed on Feb. 9, 2005, 3 pages.

U.S. Appl. No. 10/014,037, filed Dec. 10, 2001.

U.S. Appl. No. 10/653,552, filed Sep. 2, 2003.

Salama et al., Optics and Laser Technology (1999) 31:269-272.

* cited by examiner

SYSTEM AND METHODS FOR WAVEFRONT MEASUREMENT

RELATED APPLICATION INFORMATION

This application is a continuation of U.S. patent application No. 10/314,906, filed Dec. 9, 2002, which is a continuation-in-part of U.S. patent application No. 10/014,037, filed Dec. 10, 2001, now U.S. Pat. No. 6,781,681, each of which are hereby incorporated by reference in their entireties.

FIELD OF THE INVENTION

The present invention relates generally to systems and methods for measuring phase characteristics of electromagnetic wavefronts.

BACKGROUND

Measuring how a wavefront deviates from being perfectly diffraction-limited has many applications. As non-limiting examples, measuring deviations, also referred to as "aberrations", in a wavefront produced by an optical system, such as a telescope, can reveal manufacturing flaws in the system, since many optical systems, to function as best as is possible, preferably produce diffraction-limited wavefronts. By adding a component to the system that produces a wavefront that is the conjugate of the measured deviations, the system can be made to produce a more diffraction-limited wavefront and, thus, diffraction-limited performance (i.e., best possible performance).

Another example of an application where knowing the aberrations in a wavefront is useful is in correcting human vision. For instance, as noted in U.S. Pat. No. 5,963,300, by measuring deviations from the perfectly spherical in reflections of laser light from the eye of a patient, aberrations of the eye can be measured and, hence, compensated for. In the '300 patent, light that is reflected from a patient's eye is passed through two reticles, and the resulting moire shadow pattern is presented on a screen. An imaging system images the shadow on the screen onto a camera, with subsequent analysis being undertaken of the imaged shadow. The technique of the '300 patent is based on geometrical or ray-tracing analysis, which as recognized herein requires theoretical assumptions to perform the geometrical analysis that limit the amplitude of the aberrations that can be measured as well as limit the accuracy with which the aberrations can be measured.

Certain embodiments of the technology discussed below may provide solutions to one or more of these drawbacks.

SUMMARY OF THE INVENTION

A system for determining aberrations in a coherent electromagnetic wavefront includes a reticle that is positioned in the path of the wavefront, and a detector also positioned in the path. In accordance with this aspect, the light detector is located at a diffraction pattern self-imaging plane or Talbot plane relative to the reticle.

A processor may receive the output signal from the light detector and determine aberrations in the beam based thereon. The aberrations in the beam may represent aberrations in the wavefront due to the medium through which it passes, or an object from which it reflects, or the source of the wavefront itself.

In a preferred, non-limiting embodiment, the processor executes logic that includes determining a phase gradient of the wavefront phase-front, and determining coefficients of polynomials based on the phase-front gradient which quantify the aberrations. The coefficients represent aberrations. Preferably, the gradient is obtained from a frequency domain transformation of the beam, wherein the gradient is the derivative of the phase of the wavefront in directions established by the reticle orientation. In a particularly preferred, non-limiting embodiment, the derivatives are determined in at least two directions, and the coefficients are determined by fitting derivatives of a set of known polynomials (such as e.g. Zernike polynomials) to the measured gradient.

In another aspect, a method for determining aberrations in an object includes passing a light beam from the object through a reticle, and then determining derivatives that are associated with the light beam subsequent to the light beam passing through the reticle. Using the derivatives, a measure of aberrations in the object can be output.

In yet another aspect, a computer program product includes a computer readable medium having a program of instructions stored thereon for causing a digital processing apparatus to execute method steps for determining aberrations in a wavefront. These method steps include representing a diffraction pattern produced by a wavefront, and determining directional derivatives of the representation. The derivatives are fit to known polynomials or derivatives thereof to obtain coefficients of polynomials. A wavefront characterization is provided based at least in part on the coefficients, with the wavefront characterization representing aberrations in the wavefront. A frequency domain representation of the image produced by the wavefront may also be generated. Furthermore, the directional derivatives may be determined in two directions.

In still another aspect, an apparatus for detecting aberrations in an object as manifested in a wavefront includes a reticle positioned in a path of the wavefront and a light detector positioned relative to the reticle to receive the diffracted self-image that is associated with the wavefront. The self-imaging distances are at discrete distances from the reticle that are integral multiples of $$d = \left(\frac{np^2}{\lambda}\right),$$

where p is the period of the reticle and $\lambda$ is the spectral wavelength of the wavefront. A processor receives signals from the light detector that represent the self-image. The processor derives the wavefront phase gradient associated with the wavefront and uses the coefficients of derivatives of polynomials that define the wavefront to determine the wavefront aberrations.

Another aspect of the invention comprises a system for determining the shape of an electromagnetic wavefront. This system includes at least one reticle positioned in a path of the wavefront to be analyzed and at least one detector positioned to detect the wavefront passing through the reticle. The detector is substantially located at a diffraction pattern self-imaging plane relative to the reticle. The system further comprises at least one processor receiving an output signal from the light detector and calculating the shape of the wavefront based thereon.

Still another aspect of the invention comprises a method for determining aberrations in an optical system comprising at least one optical element. In this method, a test beam is propagated along a path with the optical system in the path of the test beam so as to be illuminated by the test beam. A reticle is inserted in the path of the test beam at a location with respect to the optical system so as to receive light from the optical system. The light propagates through the reticle. Directional derivatives associated with the light are determined subsequent to passing through the reticle. Additionally, the derivatives are used to output a measure of the aberrations.

Yet another aspect of the invention comprises a computer program product comprising a computer readable medium having a program of instructions stored thereon for causing a digital processing apparatus to execute method steps for determining aberrations in a wavefront. These method steps include representing at least a portion of an image produced by the wavefront and determining directional derivatives of the representation. In addition, directional derivatives are fit to known polynomials or derivatives thereof to obtain coefficients of polynomials. Furthermore, a wavefront characterization is provided based at least in part on the coefficients, the wavefront characterization representing aberrations in the wavefront.

Still another aspect of the invention comprises an apparatus for characterizing an object with a wavefront from the object. The apparatus includes at least one reticle positioned in a path of the wavefront and at least one light detector positioned relative to the reticle to receive a self-image diffraction pattern of the reticle produced by the wavefront. The apparatus further includes at least one processor receiving signals from the light detector representative of the self-image diffraction pattern and deriving derivatives associated therewith. The processor uses the derivatives to characterize the object.

Another aspect of the invention comprises a method for determining aberrations in a reflective or internally reflective object system. In this method, a light beam is passed from the object system through a reticle. This light beam produces a near field diffraction pattern at the Talbot plane. The method further comprises imaging the near field diffraction pattern at the Talbot plane and using the near field diffraction pattern to output a measure of aberrations in the light beam.

BRIEF DESCRIPTION OF THE DRAWINGS

The details of the various preferred embodiments, both as to their structure and operation, can best be understood in reference to the accompanying drawings, in which like reference numerals refer to like parts, and in which.

DETAILED DESCRIPTION OF THE PREFERRED EMBODIMENT

Figure 1:
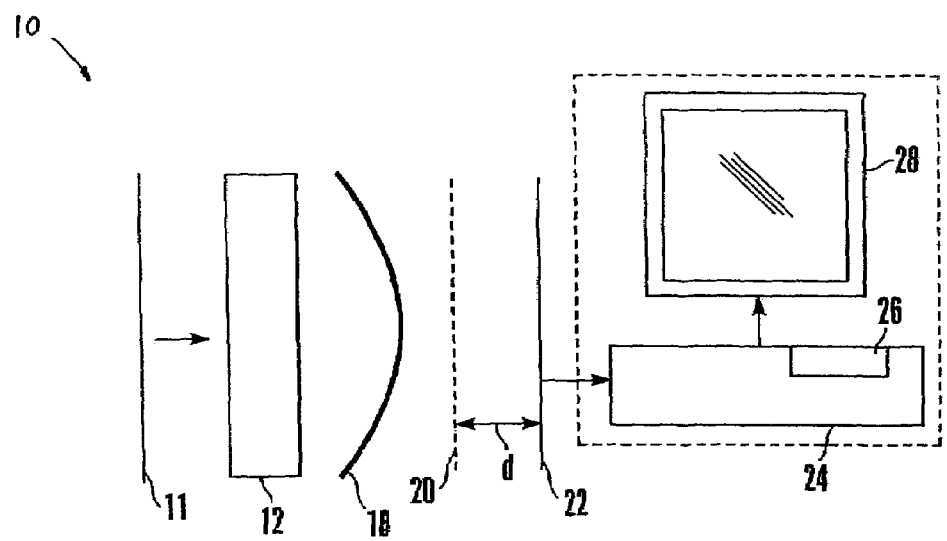
FIG. 1 is a block diagram of the one preferred embodiment of a system architecture for measuring and characterizing a wavefront.

Referring initially to FIG. 1, a wavefront sensor is shown, generally designated 10. As illustrated in FIG. 1, a reference wavefront 11 can pass through (or, be reflected from) a system or element 12 (optical or otherwise). The system or element 12 can be an optics system, such as a telescope system, or it can be a human eye, or other object having properties, e.g., aberrations or curvature, sought to be measured.

As shown in FIG. 1, a transferred wavefront 18, i.e., the wavefront 11 after having passed through or having been reflected from the system or element 12, passes through a reticle 20. For example, this reticle 20 may comprise without limitation, a diffraction grating, Ronchi ruling, or grid pattern. The reticle 20 diffracts the wavefront 18, and the diffracted wavefront self-images onto a sensor plane a self-imaging distance "d" away from the reticle 20 at which location is disposed a light sensor 22 such as but not limited to a CCD or other detector array. The self-imaging distance "d" is dependent on the spectral wavelength of the coherent wavefront and the spatial frequency of the reticle. Preferably, the CCD is within about .+−.10% or about .+−.20% of one of the self-imaging planes in the near field diffraction region.

In a non-limiting, exemplary embodiment, the wavefront incident on the imaging detector can be represented by the following diffraction equation:

$$I(\vec{r}, z) = I_0 \cos\left(\frac{\pi \lambda z}{p^2}\right) \cos\left[\frac{2\pi}{p}(\vec{r} \cdot \hat{p} - \hat{r} \cdot (\vec{z} X \vec{\nabla} w))\right]$$

where: $\lambda$ is the wavelength of the coherent wavefront, z is the propagation distance with the associated vector $\vec{z}$ in propagation direction, p is the period of the reticle (distance from the beginning of one grid line to the next grid line), r is the spatial dimension in the plane of the detector with its associated vector $\vec{r}$, $\hat{r}$ is the corresponding unit vector, $\hat{p}$ the unit vector representing the reticle orientation, and $\vec{\nabla}$ is the directional-derivative (or, gradient) of the wavefront phase "w" that is being measured. The self-imaging distance is dependent on the spectral wavelength of the coherent wavefront and the spatial frequency of the reticle and is given by:

$$d = \left(\frac{np^2}{\lambda}\right)$$

where n is the integer multiple at which distances the self-images occurs. For example, for a reticle having a grating spacing, p, of 50 micrometers (μm), this distance, d, may be between about 2.9 to 3.0 millimeters (mm) or in proximity thereto for light having a wavelength of 850 nanometers (nm). Integer multiples of this distance may be appropriate as well.

As described below, this reticle 20 may comprise rulings in orthogonal x and y directions having substantially the same period p. In other embodiments, the spacing $p_x$ and $p_y$ of the orthogonal rulings may be different for the x and y directions. Corresponding self-image planes at distances $d_x$ and $d_y$ for the different directed rulings may result. Similarly, use of more than one or two reticle patterns superimposed on another having same or different periodicity are considered possible.

The self-imaged reticle on the light sensor or detector 22 that is located at the self-image plane contains the desired information pertaining to the phase characteristics of the coherent wavefront. This information is extracted from the spatial signal collected at the sensor 22 and sent to a data processor (i.e., computer) 24 for processing in accordance with the disclosure below. To undertake the logic, the processor 24 accesses a preferably software-implemented module 26, and outputs a signal representative of the wavefront (or a conjugate thereof) to an output device 28, such as but not limited to a printer, monitor, computer, network, or other appropriate device.

In various embodiments, the beam that emerges from the reticle 20 establishes a diffraction pattern. This pattern, however, substantially cannot be discerned except at the self-image planes that are spaced integer multiples of a distance "d" from the reticle 20, as discussed above. Thus, the self image diffraction pattern can be detected by the light sensor or detector 22 that in one preferred embodiment is placed at the first (n=1) self-image plane as shown in FIG. 1, although it is to be understood that the sensor or detector 22 can be positioned at any of the self-image planes that are spaced from the reticle 20 by integer multiples of the distance "d".

Logic may be executed on the architecture shown in FIG. 1 in accordance with processes and methods described and shown herein. These methods and processes include, but are not limited to, those depicted in at least some of the blocks in the flow chart of FIG. 2 as well as the schematic representations in FIGS. 3a-3c and flow charts in FIGS. 4 and 5. These and other representations of the methods and processes described herein illustrate the structure of the logic of various embodiments of the present invention which may be embodied in computer program software. Moreover, those skilled in the art will appreciate that the flow charts and description included herein illustrate the structures of logic elements, such as computer program code elements or electronic logic circuits. Manifestly, various embodiments include a machine component that renders the logic elements in a form that instructs a digital processing apparatus (that is, a computer, controller, processor, etc.) to perform a sequence of function steps corresponding to those shown.

In other words, the logic may be embodied by a computer program that is executed by the processor 24 as a series of computer- or control element-executable instructions. These instructions may reside, for example, in RAM or on a hard drive or optical drive, or the instructions may be stored on magnetic tape, electronic read-only memory, or other appropriate data storage device that can be dynamically changed or updated.

Figure 1A:
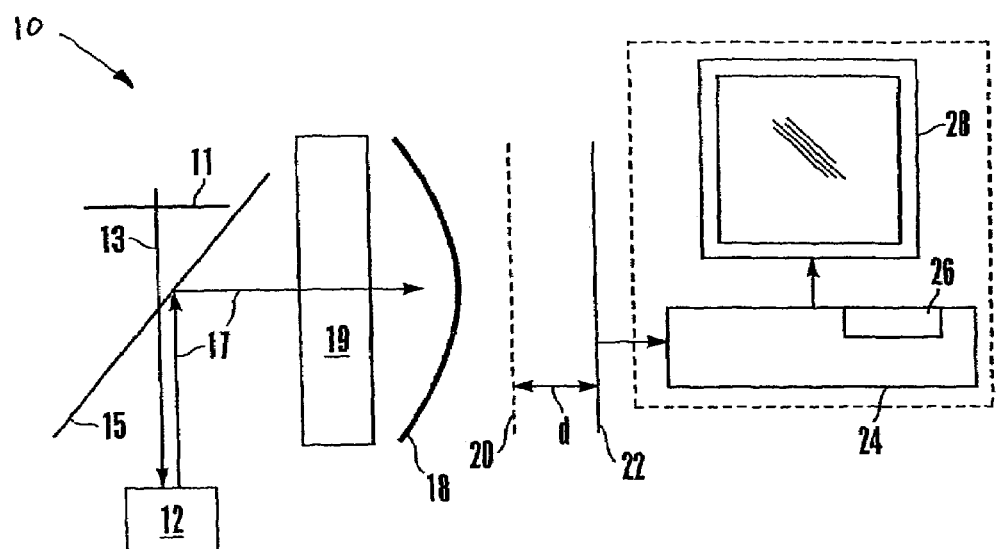
FIG. 1a is a block diagram of another implementation of the system shown in FIG. I.

FIG. 1a shows a particular non-limiting implementation of the system 10 in which the electromagnetic energy is reflected from an object or is internally reflected from within an object. Examples of applications include microwave topography of large surfaces, wherein the electromagnetic energy is microwave and the object is the surface sought to be measured; optical topography of reflective surfaces, wherein the electromagnetic energy is laser light; retinal reflection within an eye in order to measure the aberrations of the eye, and gamma ray reflection within very small objects in order to characterize mechanical or optical properties.

Accordingly, for illustration purposes FIG. 1a shows that the reference wavefront 11 passes through (or, is reflected from) a transfer (optical or otherwise) system or element 15, such as but not limited to a beamsplitter, along a propagation path 13. The wavefront 11 is incident on an object 12 such as a human eye wherein it is either reflected externally or transmits into the object 12 where it is internally reflected. The return wavefront follows along a return path 17, and can be reflected from or transmitted through the transfer system or element 15. The wavefront may then pass through an optical relay system 19. The transferred wavefront 18 passes through the reticle 20 and is processed as described above in reference to FIG. 1.

Figure 2:
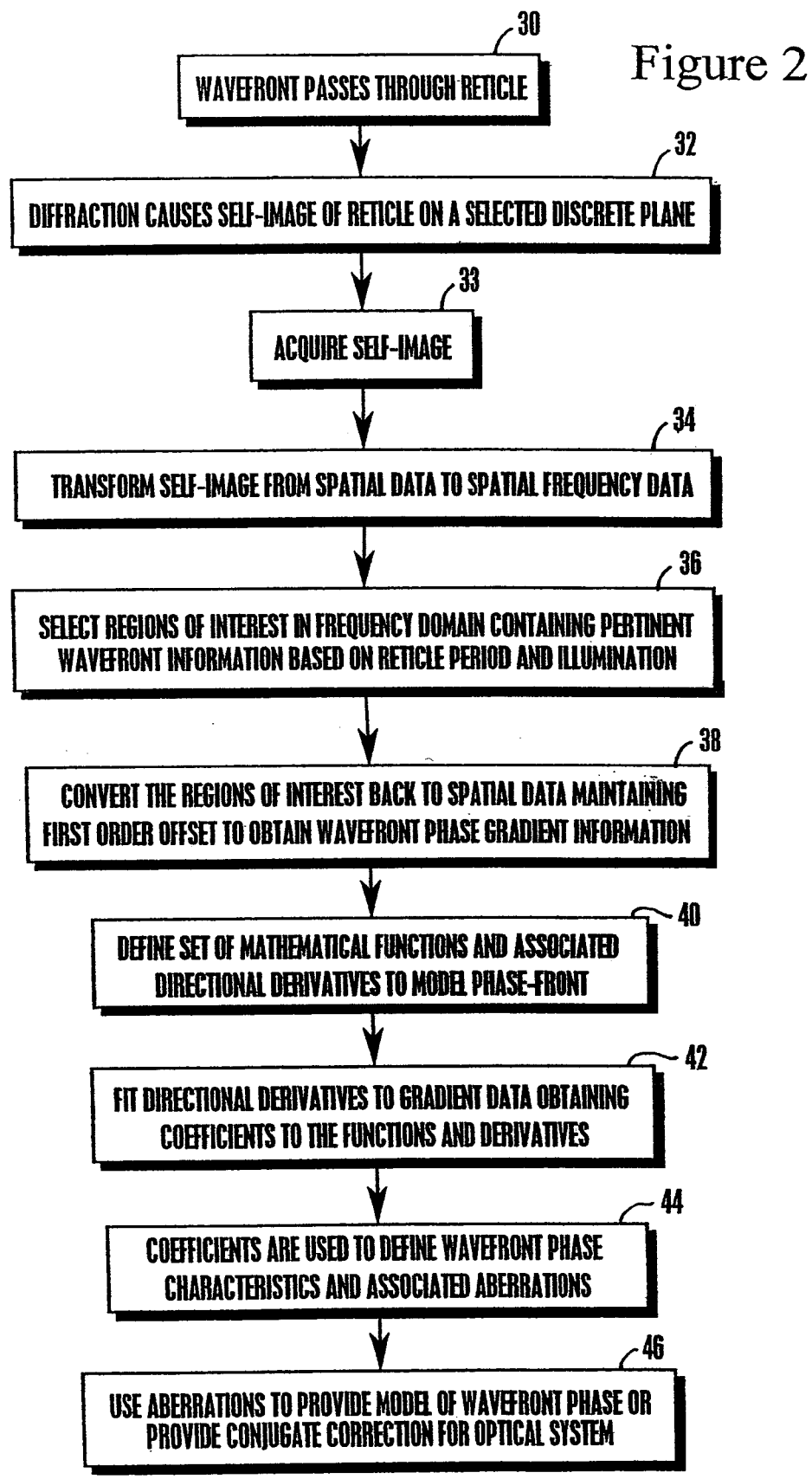
FIG. 2 is a flow chart of a preferred method of characterizing the wavefront by propagating the wavefront through a pattern and imaging the pattern at the self-image plane.

The logic of the processor 24 can be appreciated in reference to FIG. 2. Commencing at block 30 in FIG. 2, the wavefront 18 of the beam passes through the reticle 20. Diffraction effects cause a self-image of the reticle to appear at the self-image planes described above, including at the first plane located at a distance "d" from the reticle 20 where the detector 22 is positioned. The particular plane chosen for the position of the detector 22 preferably has sufficient resolution cells to resolve the diffraction pattern.

The self-image diffraction pattern caused by the beam 18 passing through the reticle 20 is acquired at block 33 by the sensor or detector 22 and is represented by the signal output by the light detector 22, as received by the processor 24. Proceeding to block 34, the signal in the spatial image domain is transformed to the spatial frequency domain. In one non-limiting embodiment, executing a Fast Fourier Transform (FFT) on the signal performs this, although it is to be understood that other mathematical transformations can be used. While FIG. 2 indicates that the FFT is implemented in software, it is to be understood by those skilled in the art that alternatively, prior to being sent to the processor 24 an optical FFT of the return beam can be made using optics such as are known in the art.

Proceeding to block 36, regions of interest in the frequency domain may be selected based on the reticle period, illumination (i.e., wavelength), and other factors discussed further below. This selection can be a priori, and need not be undertaken during measurement. Essentially, at block 36 the regions of interest for which the gradient (directional derivative) of the wavefront is to be determined are located in the spatial frequency domain and isolated.

In various preferred embodiments, the portions of the spatial frequency domain that contain the slope information and that consequently are isolated depend on the configuration of the reticle 20 and can be, e.g., represented by distributions mapped on different places on orthogonal axes in frequency space. Suitable spatial frequency domain manipulation is further illustrated in FIG. 3, discussed below.

Proceeding to block 38, an inverse transform is applied only to the isolated frequency space regions of the signal to render a spatial representation of the gradient of the wavefront preferably in the direction normal to the linear or segmented linear dimension of the reticle. Thus, if the reticle contains a singular set of linear grating lines, there will be two regions of the spatial frequency domain containing the desired information. If there are two sets of linear gratings superimposed in the reticle, the spatial frequency domain will contain four regions of interest. Each additional set of linear gratings provides more information pertaining to the wavefront gradient. In the limit, a circular grating reticle represents an infinite number of segmented linear gratings superimposed on each other. Preferably, the reticle contains two orthogonal superimposed linear grating patterns. In a non-limiting preferred embodiment, the wavefront gradient is determined in isolated regions in two directions. In a non-limiting example, when the object 12 is a human eye, the two directions are orthogonal to each other and lie in a plane defined by the front of and tangential to the patient's eye, with one of the directions extending from the center of the eye at a 45.degree. angle relative to the horizontal and tangent to the eye when the, patient is standing and facing directly forward.

If desired, in a non-limiting embodiment filtering of random background noise can be further applied by using a "computationally-implemented" matte screen by which the spatial characteristics of the self-image are enhanced and the background reduced to very low (e.g., approximately zero) frequency components in the spatial frequency domain. This principle will be further discussed in relation to FIG. 5.

Moving to block 40, a set of known functions such as polynomials (and their derivatives) is defined or otherwise accessed for the two directions mentioned above. These polynomials can be used to model the wavefront. In one preferred, non-limiting embodiment, a set of 36 Zernike polynomials are used. Then, at block 42 the derivatives of the known polynomials are fit to the derivatives (i.e., gradient) determined at block 38 using, e.g., a least squares fit or other fitting algorithm.

The outcome of the fitting step at block 42 is that each polynomial has an accompanying coefficient, also referred to as the "amplitude" of the polynomial. Each coefficient represents an aberration from the perfectly spherical in the return beam 18 and, hence, an aberration in the object 12. Consequently, at block 44 a reconstructed wavefront equation can be output (to, e.g., the output device 28) that is the set of the known polynomials with the coefficients obtained in the fitting step at block 42. At block 46, the output, and in particular the coefficients in the reconstructed wavefront equation, can be used to indicate aberrations in the original wavefront and, hence, in the object 12. Furthermore, the output can be used as a basis for implementing corrective optics for the system 12 that essentially represent the conjugate of the polynomials and/or coefficients to reduce or null out the aberrations of the object 12.

Figure 3A:
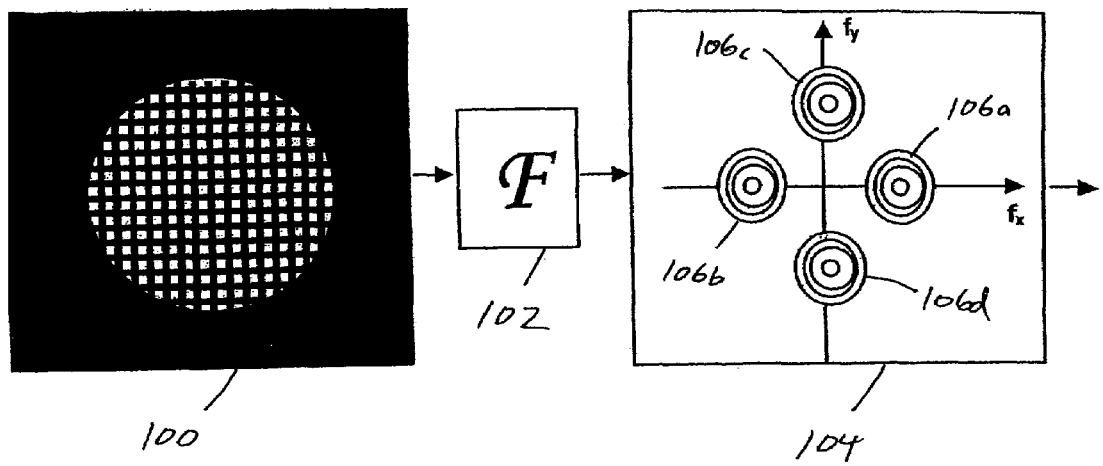
FIGS. 3a-3c are schematic diagrams illustrating one method for converting the image produced at the self-image plane into gradient information corresponding to the wavefront at that self-image plane.
Figure 3B:
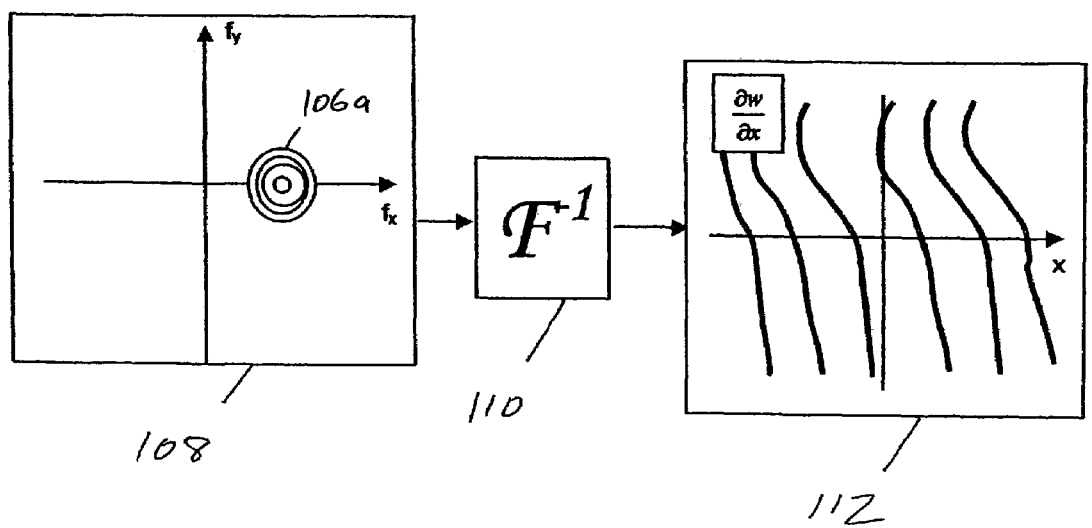
Figure 3C:
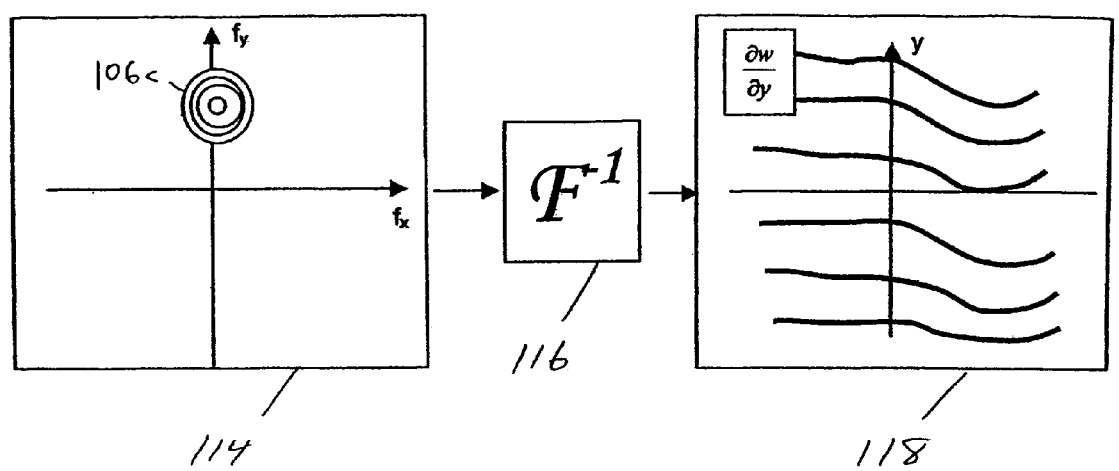

A schematic representation of an exemplary process for characterizing a wavefront gradient is depicted in FIGS. 3a-3c. A spatial image 100 of the reticle at the detector located in the self-image plane is converted by applying a Fourier transform, represented by block 102, into spatial frequency data 104. The result, is a spatial frequency pattern that includes four regions of interest 106a, 106b, 106c, and 106d which may correspond to a set of first order components in frequency space. These four regions comprise point spread functions (PSF) displaced from the origin of the spatial frequency map in directions corresponding to $\pm f_x$ and $\pm f_y$. As shown in block 108, one of these four regions is selected. In FIG. 3b, the point spread function at the $(+f_{x0}, 0)$ location is selected and the inverse Fourier transform is performed on this spatial frequency distribution as represented by block 110. In this manner, the gradient along the x direction of the wavefront at the self-image plane can be obtained as shown indicated by block 112. Similarly, FIG. 3c shows the point spread function at the $(0, +f_{y0})$ position in block 114. The inverse Fourier transform is performed on this point spread function as represented by block 116 to obtain the gradient of the wavefront in the y direction shown in block 118.

Figure 4:
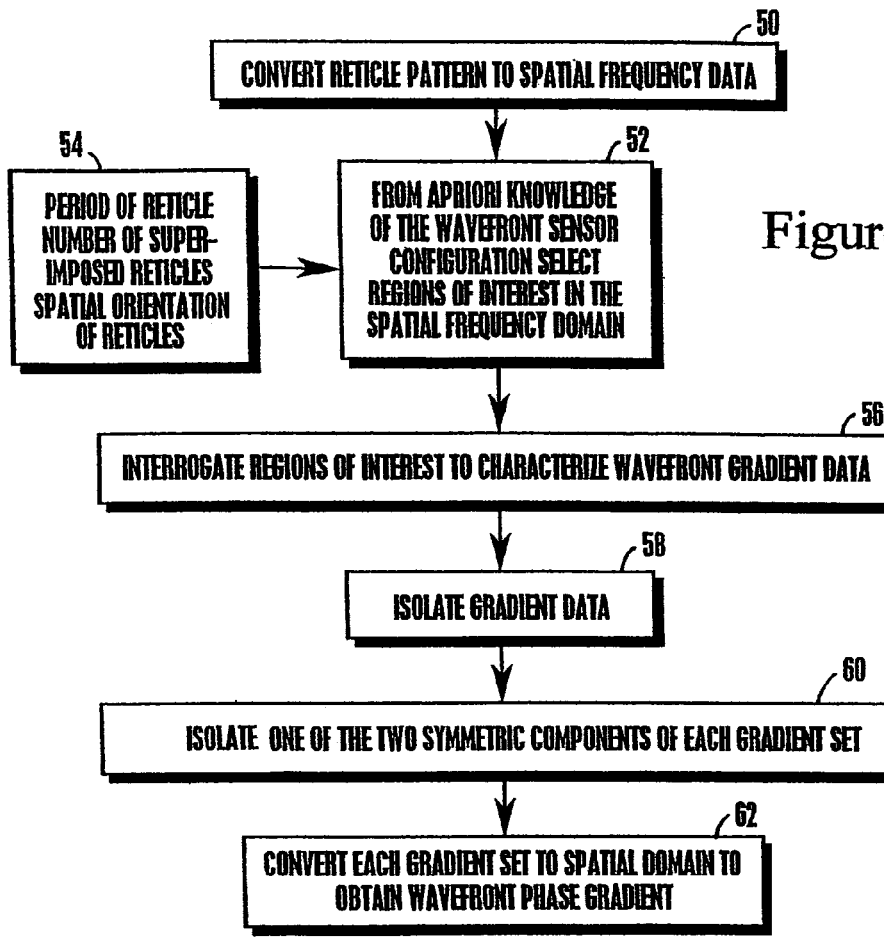
FIG. 4 is a flow chart of preferred logic for data extraction in the spatial frequency domain.

FIG. 4 shows further details of this process as discussed with respect to blocks 34, 36 and 38 in FIG. 2. At block 50 in FIG. 4, the self-image of the reticle is converted using software or optically from spatial data to spatial frequency data. As discussed above, this is preferably performed with a Fourier Transform algorithm and preferably a Fast Fourier Transform computer software algorithm (FFT). Moving to block 52, from an a priori knowledge of the system 10 configuration, regions of interest in the spatial frequency domain are selected. The a priori information is provided at block 54 as follows. The reticle 20 has (a) periodic pattern(s) in known directions. The period of the reticle, the number of superimposed reticles, and the spatial orientations of the reticle relative to the wavefront path of propagation can be used to locate these regions. Gradient data in the individual regions of interest is accessed at block 56 and isolated at block 58. This data has symmetry in the spatial frequency domain. Accordingly, in block 60 if desired only one of the symmetric data sets need be selected. Then in block 62 each set is converted back to the spatial domain. The offset of the location in frequency space of the "first order" region of interest may be used to calibrate the gradient information. This process of obtaining the wavefront phase gradient information is included in block 38 in FIG. 2.

Without subscribing to any particular scientific theories, the above operations by which the wavefront is extracted from equation (1) can be expressed in analytical form as follows. First, the non-limiting Fourier transform on the wavefront executed at block 50 in FIG. 4 can be expressed as:

$$F\{I(r, z)\} \begin{matrix} f^2 x, y & f^4 x, y \\ f^1 x, y & f^3 x, y \end{matrix} \Rightarrow F(\nabla w)$$

wherein the notation $f^1 x,y$, $f^2 x,y$, $f^3 x,y$ and $f^4 x,y$ indicates that in certain embodiments described above such as illustrated in FIGS. 3a-3c, the relevant frequency information obtained by the Fourier transform is contained in four first order distributions or point spread functions 106a, 106b, 106c, 106d located in four sectors in frequency space. Similarly, the two spatial frequency regions $f^1 x,y$ to $f^2 x,y$ and $f^3 x,y$ to $f^4 x,y$ are the two dimensional areas in the frequency domain that contain the relevant data, and $F(\nabla w)$ represents the received wavefront. The location of the point spread function may vary in different embodiments.

Then, the gradient ($\nabla w$) of the wavefront is determined by performing the inverse Fourier transform ($F^{-1}$) on equation (3) as follows:

$$F^{-1}\{F(\nabla w)\} \Rightarrow \nabla w$$

Next, the set of partial derivatives, or gradients, of the chosen polynomial set, e.g., Zernike polynomials ($\nabla Z$, or $Z_x$ and $Z_y$) are made to best approximate the gradient of the phase front ($\nabla w$) via one or more fitting algorithms such as for example a least squares algorithm. That is, $$\nabla w = \sum_{i=1}^{n} A_i Z_i$$

where, n is the number of polynomials chosen to best approximate the wavefront phase gradient, and $A_i$ is the coefficient, or amplitude, of the polynomial $Z_i$. The wavefront phase "w" can now be described as follows:

$$w = \sum_{i=1}^{n} A_i Z_i$$

The aberrations in the wavefront can be described by the values of the coefficients $A_i$.

Figure 5:
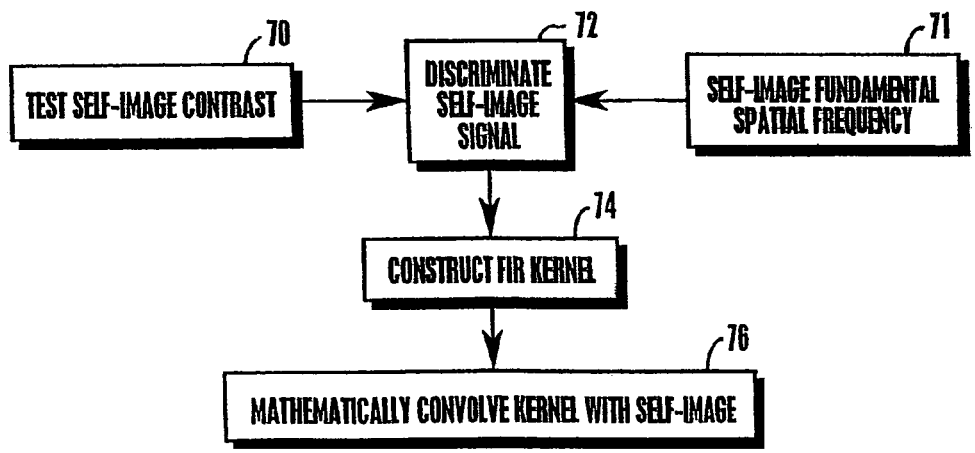
FIG. 5 is a flow chart of further logic for extraction of the desired data from spatial frequency data.

The flow chart of FIG. 5 shows the process of the "computationally-implemented" matte screen discussed above in relation to FIG. 2. In a monochromatic system a high pass spectral filter may be used to eliminate signal noise. In one exemplary embodiment, this filter is a piece of hardware called a matte screen. In many applications a matte screen is not practical to integrate into the system. Accordingly, the matte screen can be computationally implemented on the self-images.

The contrast of the image and the self-image fundamental spatial frequency are respectively received from blocks 70 and 71 and input to block 72, where the two inputs are compared to discriminate the self-image signal. If the contrast from block 70 is lower than the fundamental spatial frequency from block 71, the matte screen is implemented within block 34 of FIG. 2, with the location of the peak value in the region of interest in block 38 providing the fundamental (predominant) frequency within the self-image signal. From the peak, a finite impulse response (FIR) kernel is derived at block 74 that functions as a high-pass filter of spatial frequency data. Only frequencies higher then the designed limit will remain in the signal, and all others are eliminated at block 76 by mathematically convolving the kernel with the self-image signal.

By employing methods such as described above, a mathematical representation of the wavefront and of the aberrations can be obtained. Additionally, conjugate structures, e.g., conjugate optics, can be created to substantially offset or cancel the aberrations in the wavefront. In the case, for example, where the wavefront in the eye is measured, these conjugate optics, e.g., may take the form of a corrective lens and the method of measuring the wavefront described above can be employed to determine the appropriate prescription for such a lens.

Those skilled in the art will appreciate that the methods and designs described above have additional applications and that the relevant applications are not limited to those specifically recited above. Also, the present invention may be embodied in other specific forms without departing from the essential characteristics as described herein. The embodiments described above are to be considered in all respects as illustrative only and not restrictive in any manner.

What is claimed is:

1. A system for determining aberrations in an electromagnetic wavefront, comprising:
   at least one source of the electromagnetic wavefront directing a beam onto an object system, the object system reflecting or passing at least part of the beam to render a wavefront to be analyzed;
   a reticle positioned in a path of the wavefront to be analyzed, wherein the reticle comprises two superimposed linear grating patterns;
   at least one detector positioned to detect the wavefront passing through the reticle, the detector being located at a diffraction pattern self-imaging plane relative to the reticle; and
   at least one processor receiving an output signal from the light detector and determining at least one aberration in the wavefront based thereon, the aberration representing at least one aberration in the object system, wherein the processor executes logic to undertake method acts comprising:
   a. accessing mathematical functions to characterize the electromagnetic wavefront; and
   b. determining directional derivatives of the electromagnetic wavefront using the mathematical functions.

2. The system of claim 1, wherein at least one of the two superimposed linear grating patterns is segmented.

3. The system of claim 2, wherein the two superimposed linear grating patterns are orthogonal with respect to one another.

4. The system of claim 1, wherein the object system is an eye.

5. The system of claim 4 wherein the two superimposed linear grating patterns are orthogonal with respect to one another and lie substantially in a vertical plane, and wherein the reticle is rotated in the vertical plane at approximately a 45° angle from a horizontal plane.

6. The system of claim 4, wherein the wavefront incident on the eye is transmitted into the eye and reflected internally, creating a return wavefront, the return wavefront exiting the eye.

7. The system of claim 1, wherein the method acts include determining coefficients of polynomials based on at least one gradient of a phase-front of the wavefront, the coefficients being representative of aberrations.

8. The system of claim 7, wherein the method acts further comprise transforming the wavefront from a spatial image domain into a spatial frequency domain, prior to the act of determining coefficients.

9. The system of claim 8, wherein only selected portions in the spatial frequency domain are used to determine coefficients.

10. The system of claim 8, wherein the act of determining coefficients includes determining directional-derivatives of phases of the wavefront.

11. The system of claim 10, wherein directional derivatives are determined in at least two directions.

12. The system of claim 11, wherein the coefficients are determined by fitting derivative functions of a set of known polynomials to the derivatives obtained during the determining act.

13. A method for determining aberrations in an object system, comprising:
   a. passing a light beam from the object system through a reticle, wherein the reticle comprises two superimposed linear grating patterns:
   b. transforming a wavefront associated with the light beam from a spatial image domain into a spatial frequency domain;
   c. determining directional derivatives associated with the light beam subsequent to the light beam passing through the reticle; and
   d. determining coefficients of polynomials based on the directional derivatives, wherein the derivatives are used to output a measure of abenations in the light beam.

14. The method of claim 13, wherein at least one of the two superimposed linear grating patterns is segmented.

15. The method of claim 12, wherein the two superimposed linear grating patterns are orthogonal with respect to one another and form a checkerboard pattern.

16. The method of claim 13, wherein the act of determining derivatives includes determining derivatives of phases of the wavefront.

17. The method of claim 13, comprising determining directional derivatives in at least two directions.

18. The method of claim 13, wherein the coefficients are determined by fitting derivatives of a set of known polynomials to data obtained during the determining act.

19. The method of claim 13, wherein the object system is an eye.

20. The method of claim wherein the two superimposed linear grating patterns are orthogonal with respect to one another and lie substantially in a vertical plane, and wherein the reticle is rotated in the vertical plane at approximately a 45° angle from a horizontal plane.

21. An apparatus for detecting aberrations in an object system as manifested in a wavefront from the object system, comprising:
   a. a reticle positioned in a path of the wavefront, wherein the reticle comprises two superimposed linear grating patterns;
   b. at least one light detector positioned relative to the reticle to receive a self-image of at least one diffraction-caused pattern associated with the wavefront; and c. at least one processor receiving signals from the light detector representative of the self-image and deriving derivatives associated therewith, the processor using the derivatives to determine the aberrations, d. wherein the processor receives a frequency transformation of the wavefront and derives derivatives associated with phases of the frequency transformation, the processor determining derivatives of phases in two directions.

22. The system of claim 21, wherein at least one of the two superimposed linear grating patterns is segmented.

23. The method of claim 22, wherein the two superimposed linear grating patterns arc orthogonal with respect to one another.

24. The apparatus of claim 21, wherein the processor fits a set of known derivatives to the derivatives determined by the processor to obtain coefficients of polynomials representative of the aberrations.

25. The apparatus of claim 24, wherein only selected portions in a spatial frequency domain are used to determine coefficients.

26. The apparatus of claim 21, wherein the object system is an eye.

27. The apparatus of claim 26, wherein the two superimposed linear grating patterns are orthogonal with respect to one another and lie substantially in a vertical plane, and wherein the reticle is rotated in the vertical plane at approximately a 45° angle from a horizontal plane.

28. A method for determining aberrations in a reflective or internally reflective object, comprising;
a. passing a light beam from the object through a reticle, wherein the reticle comprises two superimposed linear grating patterns;
b. determining directional derivatives associated with the light beam subsequent to the light beam passing through the reticle; and
c. using the derivatives to output a measure of aberrations in the light beam and, hence, the object.

29. The method of claim 28, wherein at least one of the two superimposed linear grating patterns is segmented.

30. The method of claim 29, wherein the two superimposed linear grating patterns are orthogonal with respect to one another.

31. The method of claim 28, wherein the object is an eye.

32. The method of claim 31 wherein the two superimposed linear grating patterns are orthogonal with respect to one another and lie substantially in a vertical plane, and wherein the reticle is rotated in the vertical plane at approximately a 45° angle from a horizontal plane.

33. The method of claim 31, further comprising transforming a wavefront associated with the light beam from a spatial image domain into a spatial frequency domain.

34. The method of claim 33, further comprising determining coefficients of polynomials based on the direction derivatives.

35. The method of claim 34, wherein the act of determining derivatives includes determining derivatives of phases of the wavefront.

36. The method of claim 35, comprising determining directional derivatives in at least two directions.

37. The method of claim 36, wherein the coefficients are determined by fitting derivatives of a set of known polynomials to data obtained during the determining act.

38. A system for determining the shape of an electromagnetic wavefront, comprising:
a reticle positioned in a path of the wavefront to be analyzed, wherein the reticle comprises two superimposed linear grating patterns;

at least one detector positioned to detect the wavefront passing through the reticle, the detector being substantially located at a diffraction pattern self-imaging plane relative to the reticle; and at least one processor receiving an output signal from the light detector and calculating the shape of the wavefront based thereon.

39. The system of claim 38, wherein at least one of the two superimposed linear grating patterns is segmented.

40. The system of claim 39, wherein the two superimposed linear grating patterns are orthogonal with respect to one another.

41. The system of claim 40, wherein the location of the self imaging plane is a function of the wavelength of the wavefront and the spatial periodicity of the reticle.

42. The system of claim 38, wherein said diffraction pattern self imaging plane is located in the near field a longitudinal distance of approximately $$d = \left(\frac{np^2}{\lambda}\right)$$

from said reticle, wherein p is the grating spacing of the grating, $\lambda$ is the spectral wavelength of the wavefront, and n is an integer.

43. The system of claim 38, wherein the at least one processor executes logic to undertake method acts comprising determining directional derivatives of the electromagnetic wavefront.

44. The system of claim 43, wherein the method acts further include transforming a diffraction pattern of the wavefront at the detector from a spatial image domain into a spatial frequency domain, prior to the act of determining coefficients.

45. The system of claim 44, wherein selected portions in the spatial frequency domain are used to determine said coefficients.

46. The system of claim 43, wherein the method acts include determining coefficients of polynomials based on at least one gradient of a phase-front of the wavefront, the coefficients being representative of the shape of the wavefront.

47. The system of claim 46, wherein the coefficients are determined by fitting derivative functions of a set of known polynomials to the derivatives obtained during the determining act.

48. The system of claim 38, wherein directional derivatives are determined in at least two directions.

49. The system of claim 38, wherein said method acts further comprise implementing a computational matte screen for filtering out noise.

50. The system of claim 38, wherein the wavefront is reflected from an eye and the shape of the wavefront is effected by the shape of the eye.

51. The system of claim 50, wherein the two superimposed linear grating patterns are orthogonal with respect to one another and lie substantially in a vertical plane, and wherein the reticle is rotated in the vertical plane at approximately a 45° angle from a horizontal plane.

52. A method for determining aberrations in an optical system comprising at least one optical element, said method comprising:
a. propagating a test beam along a path with said optical system in said path of said test beam so as to he illuminated by said test beam;
b. inserting a reticle in said path of said test beam at a location with respect to said optical system so as to receive light from said optical system, said light propagating through said reticle, and wherein the reticle comprises two superimposed linear grating patterns; and c. determining directional derivatives associated with said light subsequent to passing through the reticle; and using the derivatives to output a measure of said aberrations.

53. The method of claim 52, wherein at least one of the two superimposed linear grating patterns is segmented.

54. The method of claim 53, wherein the two superimposed segmented linear grating patterns are orthogonal with respect to one another.

55. The method of claim 53, further comprising transforming a diffraction pattern produced by said light passing through said reticle from a spatial image into a spatial frequency distribution.

56. The method of claim 53, further comprising determining coefficients of polynomials based on the directional derivatives.

57. The method of claim 56, wherein the coefficients are determined by fitting derivatives of a set of known polynomials to data obtained during the determining act.

58. The method of claim 56, comprising determining directional derivatives in at least two directions.

59. The method of claim 56, comprising locating a light detector at a position in said path so as to receive a self-image of the reticle.

60. The method of claim 56, further comprising implementing a computational matte screen as a filter.

61. The method of claim 52, wherein the optical system is an eye.

62. The method of claim 61, wherein the two superimposed linear grating patterns are orthogonal with respect to one another and lie substantially in a vertical plane, and wherein the reticle is rotated in the vertical plane at approximately a 45° angle from a horizontal plane.

63. An apparatus for characterizing an object with a wavefront from the object, comprising:
    a reticle positioned in a path of the wavefront, the reticle comprising two superimposed linear grating patterns;
    at least one light detector positioned relative to the reticle to receive a self-image diffraction pattern of the reticle produced by the wavefront; and
    at least one processor receiving signals from the light detector representative of the self-image diffraction pattern and deriving derivatives associated therewith, the processor using the derivatives to characterize said object.

64. The apparatus of claim 63, wherein at least one of the two superimposed linear grating patterns is segmented.

65. The apparatus of claim 63, wherein the two superimposed segmented linear grating patterns are orthogonal with respect to one another.

66. The apparatus of claim 63, wherein the object is an eye.

67. The apparatus of claim 66 wherein the two superimposed linear grating patterns are orthogonal with respect to one another and lie substantially in a vertical plane, and wherein the reticle is rotated in the vertical plane at approximately a 45° angle from a horizontal plane.

68. The apparatus of claim 63, wherein the location of the reticle is related to the wavelength of the wavefront and spatial frequency of the reticle.

69. The apparatus of claim 63, wherein the processor produces frequency transformation of the wavefront to produce a distribution in frequency space and derives derivatives of phases of the wavefront from the distribution in frequency space.

70. The apparatus of claim 63, wherein the processor determines derivatives of phases in two directions.

71. The apparatus of claim 63, wherein the processor fits a set of known derivatives to the derivatives determined by the processor to obtain coefficients of polynomials representative of the aberrations.

72. A method for determining aberrations in a reflective or internally reflective object system, comprising:
    a. passing a light beam from the object system through a reticle, said light beam producing a near field diffraction pattern at a Talbot plane, wherein the reticle comprises two superimposed linear grating patterns;
    b. imaging said near field diffraction pattern at said Talbot plane;
    c. using said near field diffraction pattern to output a measure of aberrations in the light beam.

73. The method of claim 72, wherein at least one of the two superimposed linear grating patterns is segmented.

74. The method of claim 73, wherein the two superimposed linear grating patterns are orthogonal with respect to one another.

75. The method of claim 72, wherein the object system is an eye and said method is for determining abeffation in said eye.

76. The method of claim 75, wherein the two superimposed linear grating patterns are orthogonal with respect to one another and lie substantially in a vertical plane, and wherein the reticle is rotated in the vertical plane at approximately a 45° angle from a horizontal plane.

77. The method of claim 72, further comprising transforming a wavefront associated with the light beam from a spatial image domain into a spatial frequency domain.

78. The method of claim 77, wherein only selected portions in said spatial frequency domain are used to determine coefficients.

79. The method of claim 72, further comprising locating a light detector at said Talbot plane to detect the near field diffraction pattern.

80. The method of claim 72, further comprising designing coffective optics based on said measure of aberrations in said light beam so as to reduce said aberrations.

81. The method of claim 72, wherein the object system comprises an eye.

82. The method of claim 81, wherein the two superimposed linear grating patterns are orthogonal with respect to one another and lie substantially in a vertical plane, and wherein the reticle is rotated in the vertical plane at approximately a 45° angle from a horizontal plane.

83. The method of claim 72 wherein the reticle comprises a grating spacing, p, of approximately 50 micrometers, the talbot plane is located at approximately a distance, d, between 2.9 to 3.0 millimeters from the object system, or integer multiple thereof, and a wavelength of the light beam is approximately 850 nanometers.

84. The method of claim 72 wherein the object system comprises an eye, the method further comprising using the measured aberrations to determine a vision prescription for the eye.

85. The method of claim 84 further comprising creating a corrective lens that corrects for only low order aberrations of the eye.

86. The method of claim 84 further comprising creating a corrective lens that corrects for both low and high order aberrations of the eye.

87. A method for making a corrective lens for correcting abenations in an eye, comprising:

a. passing a light beam reflected from the eye through a reticle, said light beam producing a near field diffraction pattern at a self imaging plane, wherein the reticle comprises two superimposed linear grating patterns;

b. imaging said near field diffraction pattern at said self imaging plane;

c. using said near field diffraction pattern to output a measure of aberrations in the light beam; and d. using the measured abenations to create the corrective lens.

88. The method of claim 87, wherein at least one of the two superimposed linear grating patterns is segmented.

89. The method of claim 88, wherein the two superimposed linear grating patterns are orthogonal with respect to one another.

90. The method of claim 87 wherein the two superimposed linear grating patterns are orthogonal with respect to one another and lie substantially in a vertical plane, and wherein the reticle is rotated in the vertical plane at approximately a 45° angle from a horizontal plane.

91. The method of claim 87 wherein the corretive lens corrects for only low order abenations of the eye.

92. The method of claim 87 wherein the corrective lens corrects for both low and high order aberrations of the eye.

* * * * *

UNITED STATES PATENT AND TRADEMARK OFFICE
CERTIFICATE OF CORRECTION

PATENT NO. : 7,440,115 B2
APPLICATION NO. : 11/371038
DATED : October 21, 2008
INVENTOR(S) : Larry S. Horwitz Page 1 of 1

It is certified that error appears in the above-identified patent and that said Letters Patent is hereby corrected as shown below:

In Claim 20, column 10, line 54, please add the number --19-- after the word claim.

In Claim 75, column 14, line 23, after the word determining, please delete the word "abeffation" and replace with --aberration--.

In Claim 80, column 14, line 41, after the word designing, please delete the word "coffective" and replace with --corrective--.

In Claim 87, column 14, line 67, after the word correcting, please delete the word "abenations" and replace with --aberrations--.

In Claim 87, column 15, line 9, after the word measured, please delete the word "abenations" and replace with --aberrations--.

In Claim 91, column 16, line 10, after the word order, please delete the word "abenations" and replace with --aberrations--.

Signed and Sealed this

Seventh Day of July, 2009

JOHN DOLL
*Acting Director of the United States Patent and Trademark Office*